United States Patent [19]

Chmelir

[11] Patent Number: 5,264,471

[45] Date of Patent: Nov. 23, 1993

[54] PROCESS FOR THE PRODUCTION OF WATER-ABSORBING POLYMER MATERIAL WITH INCORPORATED WATER-SOLUBLE SUBSTANCES AND ITS USE FOR THE ABSORPTION AND/OR SUBSEQUENT RELEASE OF WATER OR AQUEOUS SOLUTIONS

[75] Inventor: Miroslav Chmelir, Krefeld, Fed. Rep. of Germany

[73] Assignee: Chemische Fabrik Stockhausen GmbH, Krefeld, Fed. Rep. of Germany

[21] Appl. No.: 761,073

[22] Filed: Sep. 17, 1991

[30] Foreign Application Priority Data

Sep. 19, 1990 [DE] Fed. Rep. of Germany ....... 4029591

[51] Int. Cl.$^5$ ............................ C08L 1/00; C08L 1/08
[52] U.S. Cl. ......................................... 524/35; 524/36; 524/43; 524/44; 524/54; 524/55; 524/56
[58] Field of Search ....................... 524/34, 36, 43, 44, 524/54, 55, 56, 733, 734

[56] References Cited

U.S. PATENT DOCUMENTS

| | | | |
|---|---|---|---|
| 4,058,124 | 11/1977 | Yen et al. | 524/34 |
| 4,110,431 | 8/1978 | Otia | 514/514 |
| 4,116,899 | 9/1978 | Fanta et al. | 260/17.4 GC |
| 4,666,975 | 5/1987 | Yamasaki et al. | 524/733 |

FOREIGN PATENT DOCUMENTS 0071063 2/1983 European Pat. Off. .
87/03208 6/1987 PCT Int'l Appl. .

OTHER PUBLICATIONS

European Search Report (Jan. 31, 1992).
Chemical Abstracts, vol. 103, No. 25, Dec. 23, 1985: 214126q.

*Primary Examiner*—Paul R. Michl
*Assistant Examiner*—LaVonda DeWitt
*Attorney, Agent, or Firm*—Sprung Horn Kramer & Woods

[57] ABSTRACT

The invention relates to a process for the production of absorbers for water, aqueous solutions and body liquids, the absorbers consisting of at least two components A and B, whereby component A is at least a water-swellable synthetic polymer or copolymer, and component B is at least a natural or synthetic compound being present at normal temperature as a pourable powder which is highly or at least partially soluble, in water, or as a liquid. The present invention is characterized by the fact that component B is added in the form of a powder, a liquid or as a solution to component A during the end phase of the production process thereof after a polymer reaction degree of 90%, preferably 95% is attained, that is is mixed with the polymer gel of component A and, in order to obtain a powdery, pourable end product, is dried, if necessary, and ground. The invention further relates to the use of said absorbers for the absorption and/or retention of water and/or aqueous solutions and for the subsequent controlled release of water and the substances contained in the swollen polymer gel and soluble in the aqueous medium (component B) to other bodies, preferably to plants, as nutrients for various cultures, and in the controlled dosage of nutrients and drugs.

11 Claims, No Drawings

PROCESS FOR THE PRODUCTION OF WATER-ABSORBING POLYMER MATERIAL WITH INCORPORATED WATER-SOLUBLE SUBSTANCES AND ITS USE FOR THE ABSORPTION AND/OR SUBSEQUENT RELEASE OF WATER OR AQUEOUS SOLUTIONS

The present invention relates to a process for the production of absorbing materials consisting of a combination of synthetic polymers and other substances, preferably of substances of a high or partial water-solubility which are incorporated in the polymer body. Such an absorber which rapidly absorbs water and aqueous liquids can be employed for the absorption and/or retention of water and/or aqueous solutions and for the subsequent, controlled release of water and the substances contained in the swollen polymer gel and dissolved in the aqueous medium to other bodies, for example, to culture media, it may also be used when nutrients or pharmaceuticals are to be dosed, or as water- and fertilizer-storing soil improvers.

During the last years, numerous different polymers have been developed having a high absorption capacity for water and body liquids. Cross-linked polymers and copolymers based on acrylic or methacrylic acid belong to the fully-synthetic absorbing agents described by numerous patents (German Pat. No. 244 236; German OS [Offenlegungsschrift; publication of German Pat. Appl.] Nos. 26 14 662, 26 53 135, 26 50 377, 28 13 634), or acrylamidopropane sulfonic acid copolymers (German Pat. No. 31 24 008).

Other products were produced on a starch basis, e.g., starch acrylonitrile graft polymers according to U.S. Pat. Nos. 3,997,484 and 4,155,888; or on a cellulose basis, carboxymethylcellulose according to British Pat. No. 1 159 949, and on a polysaccharide basis according to German OS 26 50 377.

The known synthetic absorbing agents are crosslinked polymers which are practically insoluble in water and at equilibrium can absorb the multiple of their weight in water or other aqueous solutions. Such products are mainly employed in the manufacture of hygienic articles (diapers, sanitary towels), but also in the cultivation of plants as water-storing soil conditioners as described, e.g., by German Pat. No. 27 37 941, or mixed with kaolin, fuller's earth, talcum, bentonite, or aluminum silicate as described by European Pat. No. 0 072 213.

Mixtures of synthetic absorbents with the fertilizers which mostly have a high or at least partial water-solubility are known, however, it is difficult to incorporate the fertilizers into the absorbent. According to European Pat. No. 0 181 983 the fertilizer is added to the acrylamide homo- or copolymer during polymerization in an amount of 10 to 50%-wt. According to European Pat. No. 0 186 721 the fertilizer is added to a highly diluted polyacrylamide gel (2%-wt.), and according to JP 60-141192 (CA 103 (25):214126 g) a powdery acrylamide/acrylic acid copolymer is dipped into a fertilizer solution and then dried. U.S. Pat. No. 4,052,190 describes a complicated mixture of fertilizer with natural rubber, such as guar gum or carob seed grain in the presence of high-molecular polycarboxylic acids and boric acid or boron salts, respectively.

The addition of a fertilizer to the monomer solution during the polymerization impairs the course of polymerization due to impurities (heavy metals) in the fertilizer. The polymerization is not completed leading to a polymer with a very high residual monomer content. Other known processes using this admixture in very high dilution are economically inefficient since high amounts of water have to be removed by drying to produce a pulverulent product.

In many applications of absorbents it is desirable to incorporate additional compounds of usually high or partial solubility into the absorbents to achieve thereby a controlled and preferably retarded release of these substances to other bodies (e.g., fertilizers to plants) when in the swollen condition.

The most simple solution of this problem, i.e., to add such a compound (referred to as "component B" hereinafter) directly to the monomer solution of component A (synthetic polymer), to homogenize it and then start the polymerization, e.g., described in European Pat. Nos.: 0 181 983 and 071 063, and in German Pat. No. 31 28 100, can only be carried out, if component B does not impair the course of polymerization.

In all other cases component B more or less affects the course of polymerization by interfering in the initiating or growth reaction (reaction with the primary radicals, transfer, termination). Even small amounts of impurities within component B which is normally harmless to the polymerization may severely influence the polymerization reaction (e.g., trace amounts of heavy metals in the conventional fertilizers) so that an even and completely performed polymerization is rendered impossible. This particularly applies to the attempts to incorporate larger amounts of component B into the polymer; they result in an incomplete polymerization reaction and an end product having a relatively high residual monomer content.

It is accordingly the object of the present invention to incorporate into the known synthetic polymers used as absorbents and having a high absorption capacity for water and aqueous liquids the highly or partially water-soluble substances in any desired, preferably larger amounts so as to obtain end products exhibiting a retarded release of the water-soluble substances to other bodies thereby maintaining the good absorption properties.

According to the present invention this object is achieved by adding component B in the form of a powder, or in dissolved or liquid form to the end phase of the manufacturing process of the synthetic crosslinked polymer A, i.e., to the end phase of polymerization in aqueous solution, and incorporating it into the synthetic polymer by subsequent drying, if necessary, under the formation of an efficient absorbing agent.

The manufacture of component A is carried out according to known methods. It may be effected discontinuously in a polymerization vessel as swollen polymer gel, or continuously on a continuous belt. According to German Pat. No. 35 44 770, e.g., the polymerization is carried out in an aqueous solution containing the water-soluble monomer and, optionally, the comonomers at a concentration of 2.2 to 8.3 mols of polymerizable double bonds per kilogram of monomer solution, in particular 3.5 to 6.25 mols (corresponding to 16 to 60%-wt., particularly 25 to 45%-wt. acrylic acid, if it is used as monomer) and within a temperature range of approximately −10° C. to 120° C.

The polymers of acrylic acid and methacrylic acid alone as homopolymer or as copolymer are preferably suitable for the use as component A, but also the polymers of other water-soluble monomers, such as acrylamide, as well as polymerizable acids and the salts thereof, in particular maleic acid, fumaric acid, itaconic acid, vinyl sulfonic acid or 2-acrylamido-2-methylpropane sulfonic acid. Further examples are hydroxyl groups containing esters of polymerizable acids, in particular the hydroxyethyl- and hydroxypropyl esters of acrylic and methacrylic acid; as well as amino-groups-containing and ammonium-groups-containing esters and amides of polymerizable acids, such as the dialkylamino esters, in particular the dimethyl-and the diethylaminoalkyl esters of acrylic and methacrylic acid, as well as the trimethyl- and triethylammonium alkylesters and the corresponding amides thereof. In addition, small amounts of cross-linking monomers, e.g., monomers having more than one polymerizable group within the molecule, are polymerized together with the above-mentioned monomers.

The above-mentioned monomers may be polymerized alone to form cross-linked homopolymers or with one another to form cross-linked copolymers.

In addition, small amounts of monomers which are slightly or even insoluble in water, such as (meth)acrylonitrile, vinyl pyridine, and vinyl acetate may be copolymerized, such as the esters of acrylic and/or methacrylic acid with $C_1$–$C_{10}$-alcohols, styrene and alkylated styrenes. In general, the proportion of water-soluble monomers is in the range of 40 to 100%-wt., relative to the total amount of monomers. The proportion of the cross-linking monomers is in the range of 0 to 20%-wt., preferably 0.01 to 2.0%-wt., relative to the total monomer amount. In general, the amount of water-insoluble, hydrophobic monomers is 0 to 40%-wt. of the monomers.

Examples of cross-linking monomers include bi- and polyfunctional monomers, e.g., amides, such as the methylene bisacryl- or -methacrylamide or ethylene bisacrylamide, in addition esters of the unsaturated mono- or polycarboxylic acids of polyols, such as diacrylates or triacrylates, e.g., butanediol- or ethylene glycol diacrylate or -methacrylate, trimethylolpropane triacrylate, as well as vinyl methacrylate and allyl compounds, such as allyl(meth)acrylate, triallyl cyanurate, maleic acid diallyl ester, polyallyl ester, tetraallyl oxiethane, triallylamine, tetraallyl ethylene diamine, allyl ester of the phosphoric acid or phosphorous acid, respectively, as well as cross-linkable monomers, such as the N-methylol compounds of amides, such as methacrylamide or acrylamide and the ethers derived therefrom.

The polymerization may be initiated by chemical catalysis and/or high-energy radiation/light. Suitable catalysts, for example, are peroxy compounds, such as potassium peroxydisulfate, hydrogen peroxide, organic peroxides, such as benzoyl peroxide, tert-butyl hydroperoxide, tert-butyl perpivalate; redox systems, such as potassium-peroxydisulfate-sodium-disulfite, hydrogen peroxide hydroxylamine chloride, or azoinitiators, such as AIBN [2,2'-azobis-(isobutyronitrile)] or 2,2'-azobis(2-amidinopropane)dihydrochloride. Examples of suitable photoinitiators include benzoin and the derivatives thereof, e.g., benzoin ether, such as benzoin-ethyl-propyl-ether, benzil and the derivatives thereof, such as benzil ketals or aryl diazonium salts, acetophenone derivatives, and others, alone or in admixtures. In general, the content of photoinitiators is in the range of 0.002 to 2.0%-wt., preferably 0.01 to 0.2%-wt., relative to the monomers used. The content of catalysts generally is in the range of 0.02 to 5.0%-wt., preferably between 0.20 to 2.0%-wt., relative to the monomers.

Inorganic and organic compounds being present as pourable powders at normal temperature and highly or at least partially soluble in water can be used as component B. Such compounds, for example, are salts of the inorganic and organic acids, preferably the salts of ammonium, sodium, potassium, lithium, calcium, magnesium, zinc, aluminum, or iron. Preferred salts of inorganic acids are the chlorides, bromides, iodides, sulfates, hydrosulfates, phosphates, hydrogen- or dihydrogenphosphates, tetraborates, nitrates, carbonates, or hydrogencarbonates; preferred salts of organic carboxylic acids are the salts of acetic acid, formic acid, adipic acid, citric acid, or tartaric acid, and as well the salts of low-molecular polymeric carboxylic-or sulfonic acids, respectively, having molecular weights between 100 and 1,000,000, preferably 2,000 to 200,000, based on homo- or copolymers of unsaturated mono- or dicarboxylic acids, sulfonic acids, aldehydes, alcohols, as well as (meth)acrylamide. The inorganic or organic acids theirselves can also be used as component B, if they are miscible with water.

Suitable inorganic acids are boric acid or phosphoric acid. Suitable organic acids are monocarboxylic acids or polycarboxylic acids, such as citric acid, tartaric acid, or adipic acid, or low-molecular polymeric carboxylic-or sulfonic acids, respectively, with molecular weights between 200 and 1,000,000 g/mol, preferably between 2,000 and 200,000 g/mol based on homo- or copolymers of unsaturated mono- or dicarboxylic acids, sulfonic acids, aldehydes, alcohols, and (meth-)acrylamide The salts of the inorganic or organic acids as well as the acids theirselves, such as the nitrates, phosphates, sulfates of ammonium, sodium or potassium, as well as phosphoric acid, which are suitable as fertilizer, are particularly preferred for the use as component B.

Additional suitable substances are: the water-soluble solid derivatives and carboxylic acid, such as amino acids, amides or diamides, preferably acetamide, urea and urea derivatives, such as thiourea, methyl- or ethyl urea.

Natural polymers based on polysaccharide may additionally be added to component B, examples thereof include modified cellulose and cellulose derivatives, e.g., alkyl-, hydroxyalkyl-, carboxymethylcellulose, gum resins, e.g., guar gum, locust bean gum, tragacanth gum, gum arabic, pectin, etc.; starch and starch derivatives, such as corn starch, grain starch, potato starch, amylose, amylopectin, dextrin, dextran, modified starch, hydroxyethyl starch, cationic starch, starch graft polymers, etc.

In addition to said natural polymers other materials with a large surface can be used to component B, e.g., fibrous material of natural fibers, preferably fibers of cotton, hemp, wool, and silk, furthermore fibrous material of cellulose fibers, such as viscose-, acetate- and triacetate fibers, or of synthetic fibers based on polyester, polyolefins, polyacrylonitrile, polyamide, polyvinyl alcohol, polyvinyl acetate, and polyvinyl chloride, polyurethane, polyvinyl urea, as well as the copolymers of these polymers. The fibrous materials may preferably be incorporated into the component in the form of short fibers having a length of 0.1 to 60 mm together with component B.

The addition of natural or synthetic fibers to the swellable polymer which contains the component B results in a more rapid absorption of water, aqueous liquids, and of the substances dissolved in water (fertilizer solution) by the swellable polymer. Said increased and, above all, quicker absorption of the liquid is due to the capillary action of the fiber proportion. By the addition of fibers (and the amount thereof) to the component B-containing polymer, an additional control of the release rate of the water-soluble fertilizer to the excess water (rain or watering), the transfer thereof to other bodies (e.g., plants), as well as of the uptake of the fertilizer solution by a partially swollen or semidry polymer becomes possible within certain limits.

Additional materials can also be used as additive, for example, odoriferous substances to perfume the final product, disinfectants, antibacterial agents, dyestuff, but also neutral fillers to extend the component A, such as wood flour, peat, ground shells of walnuts or pomaceous fruit, chitin-containing flour, sand, garden mold, or other extenders. Finally, it is also possible to add the finely ground component A in dried powder or partially swollen form together with component B to the polymer gel of component A.

The process according to the present invention consists in the fact that component B is added to the swollen polymer gel of component A as a powder or in liquid condition or as a solution during the manufacture of the synthetic polymer (component A). Advantageously, component B is added to the swollen polymer gel of component A only during the end phase of the production of component A, i.e., not before a polymer conversion of more than 90%, preferably more than 95%, and in particular more than 98% has been achieved, and is subsequently further processed.

By further processing the mixture of the two components in a mixer with a rotary stirring mechanism and, if necessary, subsequent drying the mass of polymer gel at a temperature in the range of 50° to 260° C., an end product is obtained in which component B (e.g., a fertilizer) is incorporated in the synthetic polymer in such a way that the water-soluble component B can be extracted from the swollen end product at a considerably slower rate as compared to a physical mixture of the two components.

A decelerated extraction of the fertilizer from the polymer body, i.e., a retarded release of the fertilizer to the excess water, may have very positive effects on practical applications for two reasons: First of all, in case of heavy rain, the fertilizer remains bound to the polymer body for a longer period of time and thus is available to the plants over a longer period of time, and, in the second place, the fertilizer components are washed out slowlier during rain or watering so that the ground water is not polluted to a such great extent. In both cases, an improved utilization of the fertilizer by the plants is achieved.

The incorporation of large-surface materials, such as short fibers, together with component B into the polymer gel provides additional advantages when the end product is dried. Due to the enlarged surface, the drying periods are shorter so that drying even at lower temperatures can be carried out more efficiently.

Mixing the two components may be carried out in a suitable mixer. The mixer used in the following examples consisted of a vertically or horizontally positioned metal cylinder the stirrer of which was provided with guide blades thoroughly wiping the walls of the mixer drum. Once a certain speed of the stirrer was achieved, the two components were evenly mixed over the total length of the metal cylinder and thoroughly kneaded along the walls.

A trough kneader with double-U-shaped cross-section can also be used to mix the two components A and B evenly. Within said trough, a pair of keading shafts is moving in the same or opposite direction at the same or a different speed: depending on the material to be mixed the form of the blades may also be chosen.

For this purpose, a trough kneader of Werner & Pfleiderer, Stuttgart, FRG, with toothed, oppositely running sigma-blades can be used, for example. For continuous operation, the trough kneader may be provided with a discharging cylinder and a discharge screw which either works in reverse rotation to the interior of the trough thus intensifying the mixing and kneading process, or is switched in reversed direction of the material discharge.

Examples of further suitable devices are: single-shaft mixers, such as a single-screw extruder, ko-kneaders, two-shaft mixers with twin worm operating in the same or opposite direction, conical cotruder-screw, double-shaft continuous kneader, and continuous multi-shaft devices, e.g., a four-screw extruder.

Low- or high-molecular, water-soluble or water-swellable polymers on a synthetic or natural basis (e.g., polysaccharides in dissolved or swollen condition) may additionally be used as auxiliary binding agents to support the linkage of the two components A and B. Examples of water-soluble or water-swellable polymers on a synthetic basis are polymers or copolymers based on (meth-)acrylic acid or (meth-)acrylic acid derivatives, such as the homo- or copolymers of acrylic acid, methacrylic acid, 2-acrylamido-2-methylpropane sulfonic acid, of the salts of these acids, of the acrylamide or methacrylamide with one another or with vinyl pyrrolidone and/or vinyl acetate, as well as polyvinyl alcohol.

However, it is also possible to employ low- or high-molecular polymers being present as emulsion polymers in an aqueous dispersion in the form of tiny spherical particles solubilized by an emulsifier, whereby both forms of emulsion "oil-in-water" (for water-insoluble polymers) and "water-in-oil" (for water-soluble polymers) are possible. As is generally known, the oil phase in most cases consists of organic solvents which are not miscible with water, such as aliphatic hydrocarbons (e.g., hexane, white oil).

Examples of polymers capable of forming oil-in-water emulsions include polymers of butadiene, styrene, isoprene, chloroprene, acrylonitrile, vinyl acetate, vinyl- and vinylidene chloride, alkylacrylates and alkylmethacrylates, and copolymers of these monomers with one another or with methyl styrene, isobutylene, or ethylene.

Examples of polymers which are used in water-in-oil emulsions include the above-mentioned water-soluble or water-swellable polymers or copolymers on the basis of (meth-)acrylic acid derivatives, which may be crosslinked or not.

The final product consists of the components A and B at a weight ratio of 20 to 99.8%-wt, preferably 40 to 95%-wt. of component A, and 0.2 to 80%-wt., preferably 0.5 to 60%-wt. of component B, and/or 0 to 80%-wt. of a neutral filler.

To determine the liquid absorption capacity a tea bag test was carried out. The liquid absorption of 0.2 g test substance was gravimetrically determined in a tea bag after 10 minutes (maximum value) and after centrifuging, e.g., in a commercial spin dryer at 1400 rpm, this value was then converted to 1 g of product (retention value). An aqueous 0.9% NaCl-solution was used as test liquid.

The invention is more particularly described in the following examples which are intended to illustrate, but not to limit, the present invention.

EXAMPLES 1 AND 2

In a polymerization vessel, 423 g acrylic acid, 625 g acrylamide, and 4.2 g N,N'-methylenebisacrylamide were dissolved in 2100 ml water and neutralized with 680 g potash lye (45%). The catalyst components (1.02 g azobisamidine propane dihydrochloride, 0.24 g benzil dimethyl ketal (Irgacure 651, Ciba Geigy AG), and 1.04 g t-butyl hydroperoxide, dissolved in water) were added at room temperature, and the adiabatic polymerization started with UV-light under nitrogen. The resulting polymer gel was cut into pieces and mixed at different ratios with a commercial fertilizer (17—17—17), used as component B, in a mixing device. The sequence of numbers of the fertilizer relates to the content of the individual components of 17% $K_2O$, 17% $P_2O_5$, and 17% nitrogen in the fertilizer.

Mixing and processing of the polymer gel with the component B was carried out in a mixer with rotating stirring mechanism. The device consists of a vertically or horizontally positioned metal cylinder (volume approx. 6000 ml), the agitator thereof is provided with guide blades which thoroughly wipe the walls of the mixing cylinder. After a speed of 300 rpm was achieved, a fluidized bed on the total length of the metal cylinder forms from the expelled individual particles of the mass when the rotary guide blades of the mixing device emerge. At this stage, the two components are evenly mixed and keaded.

Subsequently, the resultant mass of polymer gel was dried within a recirculating air dryer at 120° C. and then ground. The absorption capacity of the final products was determined according to the tea-bag-test method (see Table 1).

TABLE 1

| | Component A acrylic acid/ acrylamide copolymer %-wt. | Component B fertilizer %-wt. | Tea bag test values | | |
|---|---|---|---|---|---|
| | | | max-imum (ml/g) | retention (a) (ml/g) | (b) (ml/g) |
| | 100 | 0 | 40.9 | 28.0 | 28.0 |
| | 0 | 100 | 0 | 0 | 0 |
| Example 1: | 91 | 9 | 36.4 | 25.2 | 27.7 |
| Example 2: | 83 | 17 | 33.5 | 22.9 | 27.6 |

Note:
The tea-bag test values maximum and retention (a) relate to 1 g of the product composed of components A and B, retention (b) relates to 1 g of component A within the product.

The table shows that the absorption capacity of the composition (retention, maximum value) is supported by the proportion of component A only. Upon contact thereof with water, the fertilizer incorporated in the swollen polymer body is washed out at a considerably slower rate as compared to the rate upon water contact of the ordinary mixture of components A and B. In practical application, this results in the desired retarded release of the fertilizer to other bodies, e.g., to plants.

EXAMPLES 3 AND 4

According to the procedure described in Example 1, 105 g acrylic acid, 945 g acrylamide, and 4.2 g N,N'-methylenebisacrylamide were dissolved in 2100 ml water in a polymerization vessel followed by neutralization with potash lye (45%) to pH=6 and polymerization with the catalyst components as in Example 1. The resulting polymer gel was cut into pieces and mixed in portions and at different ratios with commercial fertilizer (17—17—17) (component B) in a mixer, drying at 180° C. followed.

TABLE 2

| | Component A acrylic acid/ acrylamide copolymer %-wt. | Component B fertilizer %-wt. | Tea bag test values | | |
|---|---|---|---|---|---|
| | | | max-imum (ml/g) | ret. (a) (ml/g) | (b) (ml/g) |
| | 100 | 0 | 25.5 | 16.6 | 16.6 |
| | 0 | 100 | 0 | 0 | 0 |
| Example 3: | 91 | 9 | 22.7 | 15.2 | 16.7 |
| Example 4: | 83 | 17 | 19.1 | 13.0 | 15.7 |

Note:
The tea-bag test values maximum and retention (a) relate to 1 g of the product composed of components A and B, retention (b) relates to 1 g of component A within the product.

The table shows that the absorption capacity of the composition (retention, maximum value) is supported only by the proportion of component A. Upon contact of the composition with water, the washing-out rate of the fertilizer incorporated in the polymer body is by far lower than that of the simple mixture of components A and B when in contact with water. This means in practice that the desired delayed release of fertilizer to other bodies, e.g., to plants, is achieved.

EXAMPLES 5 AND 6

A polymer gel having a content of cross-linking agents of 0.3%-wt. (relative to polyacrylic acid) was produced according to the procedure described in Example 1; it was mixed with different amounts of fertilizer and cellulose short fibers in the mixer described above and processed in the same manner as in Examples 1 and 2. A polymer mass resulted having incorporated therein cellulose fibers (length: 0.1 mm) and fertilizer, this was dried at 50° C. and examined with respect to its absorption capacity. The results are summarized in the following table.

TABLE 3

| | Component A Acrylic acid polymer %-wt. | Component B | |
|---|---|---|---|
| | | Fertilizer % wt. | Cellulose fiber %-wt. |
| | 100 | | 0 |
| Example 5: | 42.1 | 8.4 | 33.6 |
| Example 6: | 54.1 | 7.7 | 19.4 |

| | Water content %-wt. | Values of tea bag test Retention | |
|---|---|---|---|
| | | (a) (ml/g) | (b) (ml/g) |
| Example 5: | 15.9 | 11.2 | 30.3 |
| Example 6: | 18.8 | 14.2 | 32.6 |

Note:
The tea bag test values retention (a) relate to 1 g of the product composed of components A and B, retnetion (b) relates to 1 g of component A in the product.

EXAMPLES 7 TO 12

In a polymerization vessel, 370 g acrylic acid, 1.1 g N,N'-methylenebisacrylamide were dissolved in 410 ml water and partially neutralized with caustic soda lye to pH 4.5. The catalyst components (0.26 g azobisamidine propane dihydrochloride, 0.06 g benzil dimethyl ketal (Irgacure 651), and 0.26 g t-butyl hydroperoxide, dissolved in water) were added at room temperature and the adiabatic polymerization was started by UV-light. The resulting polymer gel was cut into pieces and mixed with the citric acid and mixtures of citric acid and cellulose ground fibers, respectively, in a mixer as described in Examples 1 to 3, drying at 120° C. followed. The composition of the polymer products in the individual examples and the tea bag test-values are listed in the following table:

TABLE 4

| | Component A | Component B | | Tea-bag-test-values | |
|---|---|---|---|---|---|
| | Acrylic acid polymer %-wt. | Citric acid %-wt. | Cellulose fibers %-wt. | Maximum value (a) ml/g | (b) ml/g |
| | 100 | 0 | 0 | | |
| Example 7: | 99.8 | 0.2 | 0 | 47.4 | 47.5 |
| Example 8: | 99.0 | 1.0 | 0 | 47.2 | 47.6 |
| Example 9: | 98.0 | 2.0 | 0 | 47.2 | 48.1 |
| Example 10: | 74.6 | 0.7 | 24.7 | 35.5 | 47.6 |
| Example 11: | 74.1 | 1.6 | 24.4 | 34.9 | 47.1 |
| Example 12: | 73.0 | 3.0 | 24.0 | 33.9 | 46.4 |

Note:
The tea-bag test value maximum (a) relates to 1 g of the product composed of components A and B, maximum (b) relates to 1 g of component A within the product.

EXAMPLE 13

A retarded release of the fertilizer incorporated in the cross-linked polymer was demonstrated according to the following test performance:

The polymer produced according to Example 2 with 16.7%-wt. of fertilizer (weight-in quantity 0.4 g) was mixed at a ratio of 1:1 with fine beach sand and rinsed thoroughly thrice in succession on a glass filter, each time using 20 ml dist. water. The water which was not bound in the mixture was withdrawn, and the fertilizer concentration in the eluate was determined.

As a comparison sample, 0.2 g fertilizer was also mixed with beach sand and washed through thrice in a row with 20 ml dist. water.

The results are summarized in the following table:

TABLE 5

| Thorough washing with H₂O (20 ml) | Quantity of eluate (ml) | Fertilizer concentration (mg NO₃'/l) | (%-wt.) |
|---|---|---|---|
| | | Comparison sample | |
| 1. | 20 | 5614 | 96.5 |
| 2. | 20 | 192 | 3.2 |
| 3. | 20 | samller than 20 | 0.3 |
| Total amount of fertilizer in eluate | | | 100.0 |
| Residual amount of fertilizer not washed away in sample 0 | | | |
| | | Polymer according to Example 1 | |
| 1. | 12.5 | 2250 | 38.1 |
| 2. | 11.5 | 1204 | 18.8 |
| 3. | 10.0 | 724 | 9.8 |
| Total amount of fertilizer in eluate | | | 66.7 |
| Residual aounts of fertilizer not washed away in sample 33.3 | | | |

The results reveal that nearly all of the fertilizer (96.5%-wt.) is eliminated from the sample already after the first thorough rinsing with 20 ml water. In case of the polymer according to the present invention, 62%-wt. of fertilizer remain in the swollen polymer gel after the first rinsing, after three times of washing 33.3%-wt. are still present, whereas the fertilizer has completely been washed out in the comparison sample after these three washings.

EXAMPLE 14

A delayed release of the fertilizer contained in the cross-linked polymer was demonstrated in this example, whereby the fertilizer content in the sand sample and the amounts of water for sprinkling were chosen to correspond to conditions similar to those in practice.

1. As a comparison example to evaluate a fertilizer's property of being washed out from a sample of soil (without addition of superabsorber), a commercial synthetic fertilizer 17—17—17 was mixed with fine beach sand (grain size 0.1 to 0.3 mm) first, then several times irrigated with water on a glass filter (diameter 90 mm), and the concentration of washed-out fertilizer in the filtrate determined.

Sprinkling of the sand layer was effected via a perforated plate (effect of a sprinkling can), the amount of water was chosen such that it approximately corresponded to the amount during heavy rainfall (5 to 8 l/m² within 5 min.). The sand layer of 120 g beach sand with the addition of 0.12 artificial fertilizer (0.1%-wt.) was about 1 cm high and needed 47.5 g water up to complete saturation with water. Thus a total amount of 100 ml water were used for the first irrigation so that after saturation of the sand layer with water approximately 50 ml were flown through the sand layer as filtrate. The next and the further sprinklings were carried out with 50 ml water. The amount of fertilizer was determined in the filtrate after each irrigation. After three irrigations with water, the moist sand layer was sprinkled with petri solution (0.118% solution of synthetic fertilizer 17—17—17) twice, and the amount of fertilizer in the filtrate determined again. The results are listed in the following tables 6 and 7.

TABLE 6

Eluviation of the sand layer used as soil sample consisting of: 120 g beach sand and 0.12 g synthetic fertilizer, thickness of layer: 1 cm, area: 63.6 cm².

| | | | Amount of water | |
|---|---|---|---|---|
| | Amount of water sprinkled (g) | Weight of soil (g) | in the soil sample (g) | filtrate (g) |
| 0 | — | 120.1 | — | — |
| 1. | 100 | 167.5 | 47.4 | 52 |
| 2. | 50 | 168.6 | 48.5 | 50 |
| 3. | 50 | 166.7 | 46.7 | 50 |

| | Fertilizer content | | | |
|---|---|---|---|---|
| | | | in the filtrate | |
| | in the soil sample | | individ. sample | total |
| | (mg) | (%) | (mg) | (%) |
| 0 | 120 | 100.0 | — | — |
| 1. | 15.9 | 13.2 | 104.1 | 86.8 |
| 2. | 4.1 | 3.4 | 11.8 | 96.6 |
| 3. | 2.9 | 2.4 | 1.2 | 97.6 |

TABLE 7

Irrigation of the washed-out sand layer with petri solution (0.11 solution of synthetic fertilizer 17-17-17)

| | | | Amount of water | |
|---|---|---|---|---|
| | Amount of water sprinkled (g) | Weight of soil (g) | in the soil sample (g) | filtrate (g) |
| 0 | — | 166.7 | 46.7 | — |
| 1. | 50 | 167.4 | 47.3 | 60 |
| 2. | 50 | 167.8 | 47.7 | 50 |

Fertilizer content

TABLE 7-continued

Irrigation of the washed-out sand layer with petri solution (0.11 solution of synthetic fertilizer 17-17-17)

| | in the soil sample | | in the filtrate | |
|---|---|---|---|---|
| | (mg) | (%) | individ. sample (mg) | total (%) |
| 0 | 2.9 | — | — | — |
| 1. | 47.9 | — | 13.8 | 23.5*) |
| 2. | 56.4 | — | 50.3 | 85.8*) |

*)Amount of fertilizer determined in the filtrate, relative to the amount of fertilizer in the respective petri solution used for sprinkling (50 ml)

2. In order to determine the removal of a fertilizer from a sample of soil with added superabsorber, 20%-wt. artificial fertilizer 17—17—17 were incorporated into the polymer gel according to Example the polymer gel was dried and ground. The dry, fertilizer-containing sample (0.6 g) was then mixed with 240 g fine beach sand and several times sprinkled with water as above; the amount of washed-out fertilizer in the filtrate was determined after each sprinkling. After five irrigations, the moist sand layer was subsequently rinsed with petri solution twice; the fertilizer content was determined in the superabsorber-containing sand layer.

The results are summarized in tables 8 and 9.

TABLE 8

Washing-out of a soil sample consisting of 240 g beach sand, 0.6 absorption material produced analogously to Example 1 (0.48 g polymer according to Example 1 with 0.12 synthetic fertilizer according to Example 1), layer thickness: 2 cm, area: 63.6 cm$^2$.

| Amount of sprinkled water (g) | Weight of soil (g) | Amount of water | | | |
|---|---|---|---|---|---|
| | | in the soil sample | | | filtrate (g) |
| | | total (g) | bonded$^{(a)}$ (g) | bonded$^{(b)}$ (g) | |
| 0 | — | 240.6 | — | — | — |
| 1 | 150 | 343.3 | 102.7 | 7.7 | 6.0 | 50 |
| 2 | 50 | 370.3 | 129.7 | 34.7 | 72.3 | 25 |
| 3 | 50 | 397.7 | 157.1 | 62.1 | 129.4 | 23 |
| 4 | 50 | 425.1 | 184.5 | 89.5 | 186.5 | 23 |
| 5 | 50 | 448.6 | 208.0 | 113.0 | 235.4 | 28 |

| | Fertilizer content | | | |
|---|---|---|---|---|
| | in the soil sample | | in the filtrate | |
| | (mg) | (%) | individ. sample (mg) | total (%) |
| 0 | 120 | 100 | — | — |
| 1 | 83.3 | 69.4 | 36.7 | 30.6 |
| 2 | 57.9 | 48.2 | 25.4 | 51.8 |
| 3 | 39.6 | 33.0 | 18.3 | 67.0 |
| 4 | 27.4 | 22.8 | 12.2 | 77.2 |
| 5 | 19.7 | 16.4 | 7.7 | 83.6 |

Note:
bonded$^{(a)}$ = ... water amount bonded in the soil sample by the superabsorber
bonded$^{(b)}$ = ... water amount bonded in the soil sample by the superabsorber relative to 1 g superabsorber
240 g beach sand (without superabsorber) need 95 ml water up to complete saturation with water.

TABLE 9

Sprinkling of the washed-out sand layer (Table 8) with petri solution:

| Amount of sprinkled water (g) | Weight of soil (g) | Amount of water | | | |
|---|---|---|---|---|---|
| | | in the soil sample | | | filtrate (g) |
| | | total (g) | bonded$^{(a)}$ (g) | bonded$^{(b)}$ (g) | |
| 0 | — | 448.6 | 208.0 | 113.0 | 235.4 | — |
| 1 | 50 | 434.7 | 194.1 | 99.1 | 206.5 | 63 |
| 2 | 50 | 415.8 | 172.2 | 80.1 | 167.1 | 68 |

| | Fertilizer content | | | |
|---|---|---|---|---|
| | in the soil sample | | in the filtrate | |
| | (mg) | (%) | individ. sample (mg) | total (%) |
| 0 | 19.7 | — | — | — |
| 1 | 71.3 | — | 7.2 | 12.2*) |
| 2 | 110.2 | — | 19.9 | 33.8*) |

*)Fertilizer amount determined in the filtrate, relative to amount of fertilizer in the petri solution (50 ml).
Note:
bonded$^{(a)}$ = ... water amount bonded in the soil sample by the superabsorber
bonded$^{(b)}$ = ... water amount bonded in the soil sample by the superabsorber relative to 1 g superabsorber
240 g beach sand (without superabsorber) need 95 ml water up to complete saturation with water.

The comparison of Tables 6 and 8 reveals that the eluviation of the fertilizer from the sand layer without added superabsorber amounted to 57% already after one irrigation (Table 6), after two sprinklings the fertilizer was nearly completely washed out (i.e., up to 97%). In contrast to that, the addition of fertilizer-containing superabsorber to the same sand layer resulted in a considerably slower wash-out rate (Table 8). After the first irrigation of the completely water-saturated soil sample, 70% and after the second irrigation 45% of fertilizer remained in the sand layer.

When the sand layer in which the fertilizer had been washed out was sprinkled with petri solution (Tables 7 and 8), more of the fertilizer from the petri solution remained bonded within the sand layer in which the synthetic, cross-linked polymer was present (Table 9).

The water amount of 50 ml used for sprinkling corresponds to a precipitation of 7.86 mm on the test area of 63.6 cm$^2$. The total amount of water (350 ml) used for irrigation according to Table 8 thus corresponds to rain of 55.0 mm fallen within a relatively short period of time, this, in turn, may be compared with a tropical heavy rain (35 to 50 mm precipitation within 2 to 3 hours). Heavy rainfall in our climatic conditions causes only 5 to 8 mm precipitation.

The fertilizer's property of being washed out was determined in a layer of 2 cm thickness which was sprinkled with water several times. The flow rate of water through this relatively thin layer was quite high so that swelling of the superabsorber-which depends on time-took place incompletely; this can be recognized in Table 8 (water amount bonded in the soil sample) after each respective irrigation. Nevertheless, the water amount bonded in the sample of soil clearly increases after each irrigation. This layer of 2 cm thickness represents the upper layer of the earth sample which actually is most affected by rinsing through with rain. In a test corresponding to the real conditions in plant culture with a thickness of the soil layer of more than 2 cm, the water flows through this thicker layer at a slower rate so that even more water can be absorbed by the superabsorber and less fertilizer is washed out of the soil layer.

It is understood that the specification and examples are illustrative but not limitative of the present invention and that other embodiments within the spirit and scope of the invention will suggest themselves to those skilled in the art.

I claim:

1. A process for the production of absorbing material for water, aqueous solutions and body liquids, the absorbers consisting of at least two components A and B, whereby component A is at least a water-swellable synthetic polymer or copolymer, and component B is at least a natural or synthetic compound being present at normal temperature as a pourable powder which is highly or at least partially soluble in water, or as a liquid, in which process component B is added to component A in the form of a powder, a liquid, or a solution during the end phase of the manufacturing process of component A after attainment of a polymer conversion of at least 90%, is mixed with the polymer gel of component A and, for the purpose of obtaining a powdery, pourable end product, is dried, if necessary, and ground.

2. The process according to claim 1 wherein component B is added to component A not before the end phase of component A's production process when a polymer conversion of more than 98% is attained.

3. The process according to claim 1, wherein component B is used in dried state as a powder or in an aqueous solution.

4. The process according to claim 1, wherein component A is a homo- or copolymer of acrylic acid, methacrylic acid, 2-acrylamido-2-methylpropane sulfonic acid, of the alkali- or ammonium salts of said carboxylic acids, of acrylamide or methacrylamide and the derivatives thereof, of vinyl pyrrolidone as well as the copolymers thereof with one another or only partially water-soluble monomers.

5. The process according to claim 1, wherein component A is a cross-linked polymer or copolymer, whereby difunctional or polyfunctional compounds are used as cross-linking agents.

6. The process according to claim 1, wherein component A is a copolymer of at least one of acrylic acid, methacrylic acid, 2-acrylamido-2-methylpropane-sulfonic acid, of acrylamide or methacrylamide and the derivatives thereof and vinyl pyrrolidone with vinyl acetate.

7. The process according to claim 1, wherein a fertilizer is used as the component B.

8. The process according to claim 1, wherein in addition to component B at least one polysaccharide or polysaccharide derivative or gum resin or a mixture thereof are added.

9. The process according to claim 1, wherein in addition to component B fibers of wool, silk, cotton, cellulose, viscose, acetate, triacetate, polyester, polyolefin, polyamide, polyvinyl alcohol, polyurethane, polyurea, or polyacrylonitrile are added.

10. The process according to claim 1, wherein a neutral filling agent in admixture with component B is incorporated into component A, said neutral filler being peat, sand, clay, garden mold for the cultivation of plants, other fertilizers, dyestuff, pigments, ground shells of nuts or pomaceous fruit, wood flour, chitin-containing flour, or the ground component A itself in powder or partially swollen form.

11. The process according to claim 1, wherein the end product contains 20 to 99.8%-wt., of component A, and 0.2 to 80%-wt., of component B, and 0 to 80% of a neutral filler.

* * * * *